US009249061B2

(12) United States Patent
Harman et al.

(10) Patent No.: US 9,249,061 B2
(45) Date of Patent: Feb. 2, 2016

(54) HIGHLY EFFICIENT ORGANIC FERTILIZER AND COMPONENTS THEREOF

(71) Applicant: CORNELL UNIVERSITY, Ithaca, NY (US)

(72) Inventors: Gary E. Harman, Geneva, NY (US); Xingen Lei, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 14/360,520

(22) PCT Filed: Nov. 21, 2012

(86) PCT No.: PCT/US2012/066329
§ 371 (c)(1),
(2) Date: May 23, 2014

(87) PCT Pub. No.: WO2013/078365
PCT Pub. Date: May 30, 2013

(65) Prior Publication Data
US 2014/0323297 A1 Oct. 30, 2014

Related U.S. Application Data

(60) Provisional application No. 61/563,355, filed on Nov. 23, 2011.

(51) Int. Cl.
C05C 3/00 (2006.01)
C05C 11/00 (2006.01)
(Continued)

(52) U.S. Cl.
CPC . C05B 7/00 (2013.01); C05B 17/00 (2013.01); C05C 3/00 (2013.01); C05C 5/00 (2013.01);
(Continued)

(58) Field of Classification Search
CPC ............ C05F 11/08; C05C 3/00; C05C 11/00
USPC .......................................... 71/6–10, 54, 64.1
See application file for complete search history.

(56) References Cited

U.S. PATENT DOCUMENTS 4,908,220 A 3/1990 Shih et al.
5,071,462 A * 12/1991 Kimura ................................ 71/7
(Continued)

FOREIGN PATENT DOCUMENTS

CN 101117300 A 2/2008
CN 101619006 A 1/2010
(Continued)

OTHER PUBLICATIONS

Eman F. Sharaf et al, "Keratinolytic activity of purified alkaline keratinase produced by Scopulariopsis brevicaulis (Sacc.) and its amino acids profile", Saudi Jornal of Biological Sciences (20110 18, 117-121.*

(Continued)

Primary Examiner — Wayne Langel
(74) Attorney, Agent, or Firm — LeClairRyan, a Professional Corporation

(57) ABSTRACT

The present invention relates to a fertilizer comprising at least one microbe selected from the group consisting of Trichoderma viride (NRRL B-50520), Scopulariopsis brevicaulis (NRRL B-50521), Scopulariopsis brevicaulis (NRRL B-50522), and combinations thereof, and a substrate which is acted upon by the at least one microbe to release nitrogen. The invention also relates to a fertilizer comprising at least one microbe selected from a keratin degrading microorganism and a keratin substrate which is acted upon by the at least one microbe to release nitrogen. The invention further relates to a method for enhancing growth of plants with the fertilizer, and methods of making a fertilizer. The invention further relates to an isolated Trichoderma viride strain (NRRL B-50520) and two isolated Scopulariopsis brevicaulis strains (NRRL B-50521, NRRL B-50522).

22 Claims, 4 Drawing Sheets

(51) Int. Cl.
| | |
|---|---|
| *C05B 7/00* | (2006.01) |
| *C05F 11/08* | (2006.01) |
| *C05F 1/00* | (2006.01) |
| *C12R 1/885* | (2006.01) |
| *C12R 1/645* | (2006.01) |
| *C12P 21/06* | (2006.01) |
| *C05B 17/00* | (2006.01) |
| *C05C 5/00* | (2006.01) |
| *C05C 9/00* | (2006.01) |
| *C05D 1/02* | (2006.01) |
| *C05D 3/00* | (2006.01) |
| *C05D 5/00* | (2006.01) |
| *C05D 9/02* | (2006.01) |
| *C05F 11/02* | (2006.01) |

(52) U.S. Cl.
CPC . *C05C 9/00* (2013.01); *C05C 11/00* (2013.01); *C05D 1/02* (2013.01); *C05D 3/00* (2013.01); *C05D 5/00* (2013.01); *C05D 9/02* (2013.01); *C05F 1/005* (2013.01); *C05F 11/02* (2013.01); *C05F 11/08* (2013.01); *C12P 21/06* (2013.01); *C12R 1/645* (2013.01); *C12R 1/885* (2013.01)

(56) References Cited

U.S. PATENT DOCUMENTS

| | | | | |
|---|---|---|---|---|
| 5,366,532 | A | | 11/1994 | Fages et al. |
| 5,976,210 | A | | 11/1999 | Sensibaugh |
| 6,228,806 | B1 | | 5/2001 | Mehta |
| 6,440,692 | B1 | | 8/2002 | Koyama et al. |
| 6,596,272 | B2 | | 7/2003 | Cheung |
| 8,163,672 | B2 | * | 4/2012 | Birthisel ............... 504/101 |
| 2002/0053229 | A1 | * | 5/2002 | Varshovi ................. 71/6 |
| 2005/0020449 | A1 | | 1/2005 | Blais |
| 2007/0131009 | A1 | * | 6/2007 | Westbrook et al. ........... 71/6 |
| 2008/0318777 | A1 | * | 12/2008 | Lin ................... C05D 9/02 504/117 |
| 2010/0028303 | A1 | | 2/2010 | Martin, Jr. et al. |
| 2012/0255334 | A1 | * | 10/2012 | Gans ...................... 71/6 |
| 2013/0055635 | A1 | * | 3/2013 | Harman ............... 47/58.1 R |
| 2014/0349847 | A1 | * | 11/2014 | Schrader ............... 504/100 |
| 2014/0351998 | A1 | * | 11/2014 | Gupta ............ C07K 14/415 800/278 |

FOREIGN PATENT DOCUMENTS

| | | |
|---|---|---|
| CN | 102159084 A | 8/2011 |
| EP | 0295968 B1 | 5/1994 |
| EP | 1150934 A1 | 11/2001 |
| WO | 9929177 A1 | 6/1999 |
| WO | 2010119032 A2 | 10/2010 |

OTHER PUBLICATIONS

International Search Report and Written Opinion for corresponding Application No. PCT/US2012/066329 (mailed Feb. 8, 2013) (12 pages).
ATCC Deposit No. 20900, "Trichoderma viride Persoon: Fries, anamorph," ATCC: The Essentials of Life Science Research (deposited 1991) (1 page).
ATCC Deposit No. 36840, "Scopulariopsis brevicaulis (Saccardo) Bainier, anamorph," ATCC: The Essentials of Life Science Research (deposited 1997) (2 pages).
"Microbial inoculant," Wikipedia (last modified Sep. 25, 2012) (3 pages).
"PAR4 13-0-0: Granulated Feather Meal," Bridgewell Resources (dated 2011) (2 pages).
"Natural Fertilizers: Feather Meal," North Country Organics (dated Mar. 3, 2011) (1 page).
Natural Fertilizers: Cheep Cheep 4-3-3, OMRI Listed, North Country Organics (dated Nov. 1, 2011) (3 pages).
"Container Gardening Tips: Biofertilizer" (dated 2010) (2 pages).
"Endophyte," Wikipedia (last modified Oct. 15, 2012) (3 pages).
"Biofertilizer," Wikipedia (last modified Oct. 29, 2012) (2 pages).
First Office Action and English Translation corresponding to Chinese Patent Application No. 201280062108.2 (mailed Sep. 1, 2015).

* cited by examiner

A.

B.

HIGHLY EFFICIENT ORGANIC FERTILIZER AND COMPONENTS THEREOF

This application is a national stage application under 35 U.S.C. §371 of PCT Application No. PCT/US2012/066329, filed Nov. 21, 2012, which claims the benefit of U.S. Provisional Patent Application Ser. No. 61/563,355, filed Nov. 23, 2011, which is hereby incorporated by reference in its entirety.

The subject matter of this application was made with support from the National Science Foundation, Grant No. 0945724. The government has certain rights in the invention.

FIELD OF THE INVENTION

This invention relates to highly efficient organic fertilizer and components thereof.

BACKGROUND OF THE INVENTION

Fertilizers for lawns and other purposes frequently consist of an inorganic mixture of salts that provide nitrogen, phosphorus, and potassium. Fertilizers for different purposes may be liquids or solids, and contain a wide range of nitrogen:phosphorus:potassium ("N:P:K") as well as other plant nutrients depending on the purpose for which the products are intended. Typically, fertilizer products are primarily composted of salts of inorganic compounds, and so do not qualify for organic status.

Many traditional fertilizer products function very well. However, there is increasing concern, because such fertilizers pollute water due to their release of high levels of nitrates into ground water. One fertilizer product has a formulation of 32:2:8 (% $N:P_2O:K_2O_5$). Of that 32%, the analysis on the packaging indicates that 3.8% is ammonium compounds, 53% is urea, 39% is water soluble N, and 3.8% other N. The nitrate and urea are immediately available for leaching into ground water if these compounds are not taken up by plants. Unfortunately, plants typically use only about 33% of the total nitrogen fertilizer applied (Arnall et al., "Relationship Between Nitrogen Use Efficiency and Response Index in Winter Wheat," *J. Plant Nutr.* 32:502-515 (2009)), while the remainder may be metabolized to nitrous oxides that are potent greenhouse gases or leach into soil and surface water as nitrates and nitrites, where they may be toxic (EPA limit for drinking water 10 and 1 ppm, respectively) and where they may result in areas where decay of algae and other microbes create anaerobic zones where plants, fish, and other inhabitants cannot survive. Fertilizers that do not have such adverse environmental impacts are needed.

Fertilizers for lawn uses are being modified due to regulatory concerns about eutrophication of waters. Lawn fertilizers containing phosphorus are banned by some localities for that reason. Nitrate is at least as serious a pollutant as phosphorus, and many locations, such as Long Island for example, would like to limit water pollution from this source. The seriousness of the problem can be illustrated from the following quote regarding Chesapeake Bay (Dewar et al., "Urban Fertilizers and the Chesapeake Bay: An Opportunity for Major Pollution Reduction," Executive Summary, Environment Maryland, Research and Policy Center (2011)):

> For more than 26 years, states in the Chesapeake Bay region have attempted to clean up the Bay, but it continues to choke on a lethal overdose of pollution. In order to achieve a clean, sustainable Bay, states in the Bay watershed will have to reduce nitrogen levels in Bay waters another 30 percent and reduce phosphorus by an additional 8 percent—in spite of a projected population increase of 30 percent by the year 2030. Reductions of that magnitude will only be possible if governments target all the watershed's sources of nutrient pollution.
> 
> Excess nitrogen and phosphorus, along with sediment, is a leading cause of recurring poor water quality in the Bay and the waters that feed it. About 30 percent of the Bay's phosphorus load comes from urban and suburban runoff. Those same developed lands account for 10 percent of the nitrogen-tainted runoff. Yet not nearly enough has been done to reduce nutrient runoff from developed lands.
> 
> While Maryland regulators are requiring farmers to do better at controlling nutrient-laden runoff from their fields, the state is mostly ignoring the watershed's dominant crop: grass. Throughout the Bay watershed, nearly 3.8 million acres are now planted in turf grass, and the acreage is growing as residential development expands and replaces farm fields. Turf grass is Maryland's biggest crop by far, with as much as 1.3 million acres planted in grass statewide. That compares with 1.5 million acres planted for all other crops in Maryland in 2009. Yet it is the least regulated of the state's major crops.
> 
> Turf grass becomes a pollution problem when it is covered with too much fertilizer, which contains nitrogen and phosphorus. The nutrients in fertilizer can help maintain healthy lawns, but in excess they can wash into nearby waters when it rains or snows. Excess fertilizer nutrients can also seep directly into groundwater. Whether the fertilizer is organic or chemical, its nutrients can harm the Bay and local waterways.
> 
> Tracking fertilizer use on developed land is such a low priority that the state doesn't keep statistics on it, but Maryland Department of Agriculture records show "nonfarm use" fertilizer sales are quickly catching up to farm fertilizer sales. The best estimates suggest that Maryland landowners apply at least 86 million pounds of nitrogen fertilizer to state lawns every year.
> 
> This fertilizer makes its way into rivers and the Bay. In one suburban Baltimore watershed, researchers found 56 percent of the nutrients in a local stream came from lawn fertilizer. Scientists in Texas, Wisconsin, Minnesota, Connecticut and Canada have also confirmed that pollutants in lawn fertilizer can significantly harm surface water quality.

Id. at 1-2.

Several ordinances on Long Island request "since the health of the children and citizens of [Township], their water, the environment and Long Island Sound will all benefit from the decreased use of chemical fertilizers and lawn pesticides, the Board of Selectmen urges all citizens to voluntarily refrain from the use of chemical fertilizers and lawn pesticides and urges the use of organic lawn care." Pesticides/Heribicides Model Municipal Ordinances and Regulations, Rivers Alliance of Connecticut. There is a need and potential market for organic lawn fertilizers with low likelihood to pollute water. Regulations such as the above stop short of requiring that only organic fertilizers be used, primarily because there are no non-polluting, organic, and cost-effective products that perform adequately.

Synthetic fertilizers that are primarily used are quite effective in providing quality lawns, but they are damaging to the environment. Unfortunately, as noted supra, organic fertilizers themselves are no panacea. They may also pollute waters since they still require the same amount of nitrogen to provide strong, lush lawns. Typically, current organic fertilizers have serious shortcomings. These include the failure to provide adequate green-up of lawns shortly after application, and they typically contain only 7 to 9% N of any sort. This means, that on a pound-for-pound basis, they cannot provide sufficient N for lush, green lawns unless high rates are used. In addition, to obtain adequate performance, they must be applied at 2-6 times the rate that Scotts® is applied. Thus, a bag of Scotts® fertilizer that weighs about 37 lb will fertilize 15,000 square feet and last for 1-2 months (the company advocates four applications per growing season); equivalent results with a low N organic fertilizer will require about 3 bags to deliver the same amount of N. These factors make traditional organic fertilizers inconvenient to use—customers typically don't want to carry around and spread 100-125 pounds of fertilizer when 30-35 pounds of standard synthetic fertilizers would suffice.

The fact that so much more needs to be applied makes traditional organic fertilizers uneconomical. Even if a 25 pound bag of organic fertilizer is slightly less expensive than inorganic fertilizer, the total price for more than 100 pounds is much higher. Commercial inorganic fertilizer typically retails for about $55 per bag, while the same amount of N in most organic fertilizers will cost more than $100.

The present invention is directed to overcoming these and other deficiencies in the art, and provides an answer to many of the problems of traditional fertilizer while providing several distinct paths to new and unique products that will meet the needs of both users and limit environmental problems.

SUMMARY OF THE INVENTION

The present invention relates to a fertilizer including at least one microbe selected from the group consisting of *Trichoderma viride* (NRRL B-50520), *Scopulariopsis brevicaulis* (NRRL B-50521), *Scopulariopsis brevicaulis* (NRRL B-50522), and combinations thereof. The fertilizer also includes a substrate which is acted upon by the at least one microbe to release nitrogen.

Another aspect of the present invention relates to a method of enhancing growth of plants. The method includes providing a fertilizer comprising at least one microbe selected from the group consisting of *Trichoderma viride* (NRRL B-50520), *Scopulariopsis brevicaulis* (NRRL B-50521), *Scopulariopsis brevicaulis* (NRRL B-50522), and combinations thereof; and a substrate which is acted upon by the at least one microbe to release nitrogen. The method further includes contacting the fertilizer with plants or plant seeds under conditions effective to enhance the growth of the plants or plant seeds compared to plants or plant seeds to which the fertilizer was not applied.

The present invention also relates to a fertilizer that includes at least one microbe selected from a keratin degrading microorganism and a keratin substrate which is acted upon by the at least one microbe to release nitrogen.

Another aspect of the present invention relates to a method of making a fertilizer comprising amino acids and ammonia. This method includes providing at least one microbe selected from the group consisting of *Trichoderma viride* (NRRL B-50520), *Scopulariopsis brevicaulis* (NRRL B-50521), *Scopulariopsis brevicaulis* (NRRL B-50522), and combinations thereof and providing a substrate which is acted upon by the at least one microbe to release nitrogen. The method further includes contacting the at least one microbe and the substrate under conditions effective to cause the at least one microbe to act on the substrate and produce a liquid suspension comprising amino acids and ammonia.

The present invention also relates to an isolated *Trichoderma viride* strain deposited with Agricultural Research Service Culture Collection under number NRRL B-50520.

Another aspect of the present invention relates to an isolated *Scopulariopsis brevicaulis* strain deposited with Agricultural Research Service Culture Collection under number NRRL B-50521.

Another aspect of the present invention relates to an isolated *Scopulariopsis brevicaulis* strain deposited with Agricultural Research Service Culture Collection under number NRRL B-50522.

This invention relates to the development of highly effective organic fertilizers that can be used for many purposes and can minimize or eliminate groundwater pollution from nitrates. It includes the identification of slow-release nitrogen forms and methods of their use. It also includes microbial agents that can degrade complex forms of nitrogen, especially proteins produced from agricultural waste products, and release plant-available nitrogen in the soil or in fermenters. It describes the use of microbes that are endophytic plant symbionts that enhance the activity of the fertilizers described herein and also enhance plant growth and performance. The fertilizers are efficient methods of delivery of these organisms.

The requirements for user-acceptable and nonpolluting fertilizers are several. First, there is a need for a universally applicable mechanism whereby plants can take up N fertilizer more efficiently. One method to accomplish this is through the use of endophytic plant symbiotic fungi or bacteria that increase plants' abilities to use nitrogen fertilizer more efficiently ("nitrogen use efficiency" or "NUE"). NUE can be induced by increasing plant root growth and by physiological changes in plants. A number of microorganisms are potentially useful in this regard. For example, these include bacteria designated as Plant Growth Promoting Rhizobacteria ("PGPR"), the Basidiomycete Piriformospora indica, and mycorhizzal fungi such as those in the genus *Glomus*. Other examples include *T. harzianum* strain RR17Bc (ATCC accession PTA 9708), *T. harzianum* F11Bab (ATCC accession PTA 9709), *T. atroviride* strain WW10TC4 (ATCC PTA accession 9707), and *T. vixens* strain 41 (ATCC accession 20476)). These same fungi also induce numerous other beneficial changes in plants such as resistance to disease, resistance to abiotic stresses like drought and salt, and increased abilities of plants to photosynthesize, thereby providing additional benefits to plants.

For lawns, the present invention provides an organic fertilizer that has an analysis of 12-16:0-10:5-15 that is functionally equivalent to a widely sold inorganic lawn fertilizer that has an analysis of 30:2:8 ($N:P_2O_5:K_2O$). Also described is a prototype process of producing a granular fertilizer suitable for dispersal in standard drop or broadcast fertilizer spreaders that contains the organisms that are claimed in this invention. Also described is a method for producing a powdered formulation that can be incorporated into potting media, applied to furrows and the like, and also a liquid organic fertilizer formulation process. The result is a new fertilizer, which may be classified as organic.

Another useful attribute that can be provided by components of fertilizers is the slow release of nutrients. Fertilizers that are composed simply of soluble salts release their nutrients rapidly and provide a flush of nutrients into ground water, and they rapidly become pollutants. As described herein, microorganisms, particularly selected *Trichoderma* strains, can markedly enhance plant growth, improve resistance to abiotic stresses, increase plant nitrogen use efficiency, increase root growth and development, and markedly enhance general plant performance. It is highly advantageous to incorporate such beneficial microbes directly onto or into fertilizers so that the benefits of both the fertilizers and beneficial microbes can be conveniently applied at the same time and in the same product. However, the high salt content of most synthetic fertilizers will severely damage or kill applied microbes contained within or on the fertilizers. This invention describes fertilizers and methods of making fertilizer granules that are composed primarily of proteins that are not injurious to microbial agents. Pollution is particularly likely if fertilizers are overapplied, if there is excessive water from rain or irrigation, or when they are applied to soils that are sandy and that leach nutrients. Since it cannot be anticipated where or how fertilizers are applied, nitrogen may be in a form that is released slowly, so that plants can take up more of the applied nutrients as it is released slowly rather than all at once. There are two basic methods of approach. First, a standard process in the industry is to produce nitrogen in various forms that release nitrogen slowly. There are a number of slow release forms of nitrogen in commercial trade today. These include urea-formaldehyde, methylene urea, sulfur coated urea, and others. These are well known in the field, see for example U.S. Pat. No. 8,182,572 to King et al, which is hereby incorporated by reference in it entirety. Second, there are various complex forms of nitrogen, usually in the form of proteins, manures or composts. These materials release their nitrogen slowly, as a consequence of microbial activity.

"Organic" materials may be certified, and the rules pertaining to them are agency dependent. The Organic Materials Research Institute ("OMRI") certified products according to their own specifications. OMRI is a private agency with well established certification. Many, but not all agricultural waste products such as composts, manures, and the like, can be certified, but the requirements by which they are made are relatively stringent. A few well-defined chemicals can be used, but their uses are strictly governed. For example sodium nitrate is acceptable only if it is a mined form (called Chilean nitrate) and not a manufactured version, and even with this material its use is limited. Another, near-organic certification is the USDA BioPreferred product listing. Products with this designation are required to be derived from bio-based farm products to a certain percentage of the total. The minimum content of farm-derived products for fertilizers is 71%. This can include many of the same materials that are listed by OMRI, but there are exceptions. For example, peat moss is eligible for certification by OMRI, but not by the BioPreferred program. Composts, manures, sources of protein from both farm animals and plants are acceptable for both. One significant difference is that the OMRI registered products have to be 100% of their certified products, but for BioPreferred, up to 29% can be other than products on the BioPreferred list. Thus, it is possible to use some of the synthetic slow-release synthetic nitrogen forms with a BioPreferred product, but not with an OMRI-labeled product.

The present invention describes microbes (i.e., fungi) that effectively degrade keratin in feathers/feather meal. These microbes rapidly release amino acids and ammonia from feather meal in semi-solid media. For example, inoculum of the fungi has many uses and can be prepared as a dry spore preparation or as a liquid formulation. The present invention also describes a method for producing a granule that can be broadcast, with or without a coating of microbes, or with or without having the microbes incorporated within the granule, that provide a slow-release microbially-activated release of nitrogen for plant growth, especially when combined with other beneficial fungi. The combination of microbially-activated nitrogen systems release almost no nitrates into soils and, therefore, there will be little or no release of nitrates into ground water. This environmental advantage will be even greater if the microbial release of N is combined with other microbes that increase root growth and improve plant nitrogen use efficiency. Further, the same invention, with minor modifications, can be used to produce a soluble source or amino acids and ammonia that are highly beneficial for use as a plant fertilizer.

The present invention satisfies the needs created by conventional fertilizers, by providing a system or systems comprising fertilizers with specific compositions and functions combined with microorganisms that degrade complex proteinaceous substrates to provide nutrients, especially nutrients to growing plants. It also includes microorganisms (i.e., endophytic plant symbionts) that enhance plant growth and performance and provide other advantages to plant growth. The fertilizers of the present invention are excellent delivery agents for these organisms.

The present invention is expected to provide revolutionary benefits to the fertilizer industry. First, the fertilizer of the present invention provides, for the first time, a totally organic or biopreferred fertilizer that performs as well as standard widely-sold inorganic fertilizers. It also serves as a fertilizer that is as convenient and easy-to-use as conventional inorganic fertilizers and is useful as a lawn fertilizer that has greatly reduced pollution of ground and surface waters with nitrates. The fertilizer of the present invention also provides a method to produce a new class of organic soluble fertilizers that include immediately available nitrogen for plant growth in the form of amino acids and ammonia. The only product available to organic (OMRI certified) growers that contains immediately available nitrogen is Chilean nitrate, and its use is limited by OMRI rules, and it may be banned from organic use in the near future. A mixture of amino acids and ammonia would be a very useful new product that can be used either as a component of other fertilizers or else as a liquid stand-alone fertilizer. The present invention describes, for the first time, a method of deriving an OMRI registerable mixture of amino acids and ammonia and the composition of such as product. The focus is on lawn fertilizers, which are probably the most demanding, and perhaps the materials used in the greatest amounts, but the principles and developments are equally applicable to fertilizers for other applications. Products with these capabilities do not currently exist.

BRIEF DESCRIPTION OF THE DRAWINGS

In FIG. 2A, the treatments used were PT (organic fertilizer, NRRL B-50521, and K1-K4, which included *T. harzianum* strain RR17Bc (ATCC accession PTA 9708), *T. harzianum* F11Bab (ATCC accession PTA 9709), *T. atroviride* strain WW10TC4 (ATCC PTA accession 9707), and *T. virens* strain 41 (ATCC accession 20476)); STB (Scotts® Turf Builder®); P (organic fertilizer with NRRL B-50521); and C (untreated control). In FIG. 2B, the treatments used were PT (organic fertilizer, NRRL B-50521, and K1-K4, as described supra); OFC (organic fertilizer granules without any fungi); and P (organic fertilizer with NRRL B-50521).

DETAILED DESCRIPTION OF THE INVENTION

Figure 1:
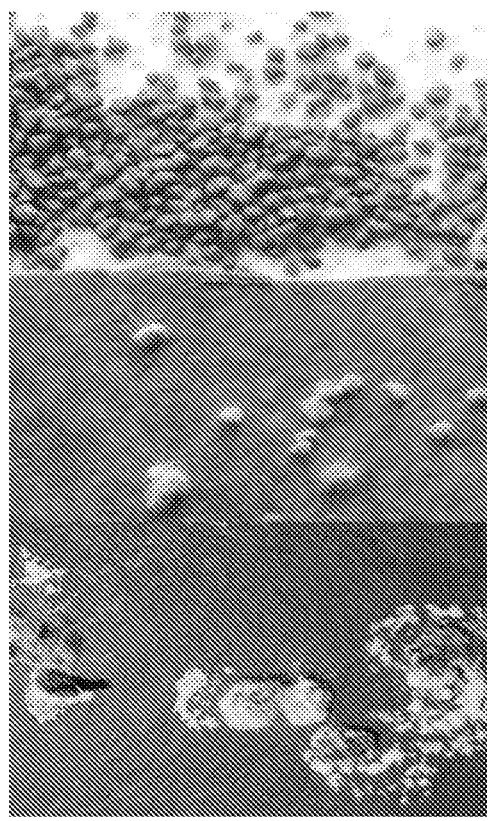
FIG. 1 shows dry granules prepared using a feather powder-gelatin mixture coated with feature degrading microbes, before and after moistening for two days. The fungi that were coated on the outside of the granules grew moderately. The granules were modified by the addition of media that would support the growth of *Trichoderma* rapidly and abundantly. The dry granules are approximately 2 mm in diameter.

The present invention relates to a fertilizer including at least one microbe selected from the group consisting of *Trichoderma viride* (NRRL B-50520), *Scopulariopsis brevicaulis* (NRRL B-50521), *Scopulariopsis brevicaulis* (NRRL B-50522), and combinations thereof. The fertilizer also includes a substrate which is acted upon by the at least one microbe to release nitrogen.

The present invention can be carried out with all types of substrate that is acted upon by a microbe to release nitrogen, including hair, hooves, and feather. In one embodiment, the substrate is any protein selected from the group consisting of feather, feather meal, and a derivative of urea. Any type of feather may be employed, including but not limited to chicken, turkey, and duck feather. The present invention is applicable to the degradation and utilization of all substrate materials that release nitrogen.

Any of a number of organisms or beneficial microbes can be added to the fertilizer of the present invention. These include those strains described in WO 2010/091337 to Harman; Harman, "Multifunctional Fungal Plant Symbionts: New Tools to Enhance Plant Growth and Productivity," *New Phytol.* 189:647-49 (2011); Lorito et al., "Translational Research on *Trichoderma*: From 'Omics to the Field," *Annu. Rev. Phytopathol.* 48:395-417 (2010); Shoresh et al., "Induced Systemic Resistance and Plant Responses to Fungal Biocontrol Agents," *Annu. Rev. Phytopathol.* 48:21-43 (2010), which are hereby incorporated by reference in their entireties. Other beneficial organisms include mycorrhizal fungi, plant growth promoting rhizobacteria, azospirillum, and nitrogen fixing rhizobia. These organisms have very many useful attributes. The fungi change gene expression and cause plants to exhibit increased resistance to disease-causing pathogens ("resistance to biotic stresses"), exhibit increased resistance to environmental stresses such as resistance to drought, salt or temperature ("resistance to abiotic stresses"), and increase the efficiency of uptake of nitrogen ("improved nitrogen use efficiency ['NUE']"). Beneficial microbes and endophytic plant microbes of the present invention may provide improved nitrogen use efficiency. Beneficial microbes may be formulated or mixed to prepare granules or liquid suspensions. These can be mixed directly into soils or potting mixes. The term soil in this specification is used to include any medium capable of supporting the growth of plants and, therefore, includes common soil, humus, manure, compose, sand, and the like, and also artificially created plant growth media. The preparations are then mixed into the soil or planting mix volume for greenhouse applications or into the upper volume of field soil (Harman, G. E., "The Dogmas and Myths of Biocontrol. Changes in Perceptions Based on Research with *Trichoderma harzianum* T-22," *Plant Dis.* 84:377-393 (2000), which is hereby incorporated by reference in its entirety). Equipment and procedures for such applications are well known and used in various agricultural industries. In one embodiment of the present invention, the fertilizer further comprises a supplemental microbe in the form of a *Trichoderma* species. The *Trichoderma* species can be selected from the group consisting of *Trichoderma vixens, Trichoderma harzianum, Trichoderma atroviride*, and combinations thereof.

*Trichoderma* grows intercellularly in the root epidermis and cortex and induces the surrounding plant cells to deposit cell wall material and produce phenolic compounds. This plant reaction limits the *Trichoderma* growth inside the root (see Yedidia et al., "Induction and Accumulation of PR Proteins Activity During Early Stages of Root Colonization by the Mycoparasite *Trichoderma harzianum* Strain T-203," *Plant Physiol. Biochem.* 38:863-873 (1999), which is hereby incorporated by reference in its entirety). Endophytic plant symbionts have much longer periods of efficacy since they have the ability to grow with plants and in the environment; therefore if conditions are favorable for them, they may have effects for weeks or months. These organisms may develop on or in plant roots and provide benefits to plants for at least the life of an annual crop (Harman, G. E., "Myths and Dogmas of biocontrol. Changes in Perceptions Derived from Research on *Trichoderma harzianum* T-22," *Plant Dis.* 84:377-393 (2000) and Harman et al., "Changing Paradigms on the Mode of Action and Uses of *Trichoderma* spp. for Biocontrol," *Outlooks Pest Manag.* 19:24-29 (2008), which are hereby incorporated by reference in their entirety). The establishment of living hyphae of the beneficial organisms in the root cortex results in chemical communication with the plant. In some embodiments, the fertilizer contains other supplemental microbes, such as those selected from the group consisting of Piriformospora indica, a plant growth promoting rhizobacteria, mycorrhizal fungi, and combinations thereof.

As a consequence, reprogramming of plant gene expression occurs, and numerous benefits to the plant result. This capability of growing on, or conidial germination on, root surfaces makes possible many kinds of application methods. These include, but are not limited to, seed treatments, application to soils or planting mixes as drenches that penetrate the soil volume and in furrow application at the time of planting, broadcast or spray applications to soil surfaces containing roots. It also permits the use of very small amounts of inoculum (10 s of g/ha) applied as a seed treatment, but that then results in subsequent proliferation of the organism on roots, causing season-long effects, including plant protection, greater root proliferation and enhanced exploration of the soil by roots (Adams et al., "*Trichoderma harzianum* Rifai 1295-22 Mediates Growth Promotion of Crack Willow (*Salix fragilis*) Saplings in Both Clean and Metal-contaminated Soil," *Microbial. Ecol.* 54:306-313 (2007); Harman, G. E., "Myths and Dogmas of Biocontrol. Changes in Perceptions Derived from Research on *Trichoderma harzianum* T-22," *Plant Dis.* 84:377-393 (2000); Harman et al., "Changing Paradigms on the Mode of Action and Uses of *Trichoderma* spp. for Biocontrol," *Outlooks Pest Manag.* 19:24-29 (2008); and Harman et al., "*Trichoderma* Species—Opportunistic, Avirulent Plant Symbionts," *Nature Rev. Microbiol.* 2:43-56 (2004), which are hereby incorporated by reference in their entirety).

*Trichoderma* strains suitable for the present invention (e.g., *Trichoderma viride, Trichoderma vixens, Trichoderma harzianum*, and *Trichoderma atroviride*) are strains with strong abilities to colonize roots. This ability is known as rhizosphere competence, which is used herein to describe those organisms capable of colonizing the root surface or the surface plus surrounding soil volume (rhizoplane and rhizosphere, respectively), when applied as a seed or other point source at the time of planting in absence of bulk flow of water. Thus, the organisms of the present invention have the physiological and genetic ability to proliferate in and on the root as it develops. Rhizosphere competence is not an absolute term, and degrees of this ability may occur among strains (Harman, G. E., "The Development and Benefits of Rhizosphere Competent Fungi for Biological Control of Plant Pathogens," *J. Plant Nutrition* 15:835-843 (1992); U.S. Pat. Nos. 4,996,157 and 5,165,928 to Smith, which are hereby incorporated by reference in their entirety). Procedures for measuring rhizosphere competence are known to those skilled in the art (Harman et al., "Combining Effective Strains of *Trichoderma harzianum* and Solid Matrix Priming to Improve Biological Seed Treatments," *Plant Disease* 73:631-637 (1989); Harman, G. E., "The Myths and Dogmas of Biocontrol. Changes in Perceptions Based on Research with *Trichoderma harzianum* T-22," *Plant Disease* 84:377-393 (2000); Kloepper et al., "A Review of Issues Related to Measuring Colonization of Plant Roots by Bacteria," *Can. J. Microbiol.* 38:1219-1232 (1992), which are hereby incorporated by reference in their entirety).

The fertilizer of the present invention may be in granule, pellet, dust, powder, slurry, film, and/or liquid suspension form. In one embodiment, the fertilizer is in the form of a granule or pellet which contains gelatin as a solidifying agent. The gelatin may be 5-20 wt % of the granule or pellet, or more preferably, 7-8 wt % of the granule or pellet. In another embodiment, the fertilizer includes at least $10^4$ colony forming units/g ("cfu") of the at least one microbe in the substrate. In yet another embodiment, the fertilizer is in the form of a liquid suspension including amino acids and ammonia. The microbes of the present invention grow, and so by weight their quantities are vanishingly small. $10^4$ cfu is equivalent to a proportion of the microbial formulation as little as one part in $10^7$ of the substrate. However, the formulation can be made in a number of different ways and, therefore, can easily be a 100× variation in the concentration of the *Trichoderma* or other microbe in the granule or pellet.

The fertilizer of the present invention also contemplates the addition of a supplemental source of nutrients. These include, for example, soil, water, urea, ammonium nitrate, sources providing nitrogen, phosphorous, potassium, calcium, magnesium, sulfur, and other micronutrients. There are at least sixteen chemical elements known to be useful in a plant's growth and survival. The sixteen chemical elements are divided into two main groups: non-mineral and mineral. The non-mineral nutrients include hydrogen (H), oxygen (O), and carbon (C) and are found in the air and water. The remaining 13 nutrients are minerals, which come from the soil, and are dissolved in water and absorbed through a plant's roots. The mineral nutrients are further divided into two groups: macronutrients and micronutrients. Macronutrients include but are not limited to N, P, S, K, Ca, Mg, Na, and Si. Micronutrients include, but are not limited to, Fe, Mn, Cu, Zn, Mo, B, and Cl. Micronutrients are needed in only very small (i.e., micro) quantities. These nutrients and their benefits to plants would be well known to a person of skill in the art. The fertilizer of the present invention may also contain a soluble nitrogen source selected from the group consisting of nitrate, ammonia, ammonium salts, amino acids, urea, fish meal or extract, compost extract, kelp extract, shrimp extract, shellfish extract, and combinations thereof.

The substrate of the present invention can be blended with other sources of plant nutrients, including potassium, phosphorus, iron or minor nutrients.

In one embodiment, the fertilizer further comprises a non-proteinaceous binding agent selected from the group consisting of dextrans, starches, polyvinylchloride, and combinations thereof.

In another embodiment, the fertilizer may include a source of phosphorus selected from the group consisting of rock phosphate, sodium phosphate, potassium phosphate, bone meal, and combinations thereof.

In yet another embodiment, the fertilizer may include a source of potassium selected from the group consisting of potassium chloride, potassium phosphate, potassium sulfate, Jersey green sand, organic sources of potassium, animal manure, and combinations thereof. For organic uses, sources of potassium include Jersey green sand, and organically listed potassium sulfate and chloride.

The fertilizer may, alternatively, include minor nutrients selected from the group consisting of salts, substances that contain iron, cobalt, manganese, magnesium, copper, calcium, boron, zinc, and combinations thereof. These are readily available from a variety of sources.

Sulfur is already present in the amino acids contained in the substrate, including, for example, feather meal. Useful fertilizers may be prepared with a variety of N:P:K ratios with or without other nutrients by blending or addition of other sources of organic substrates other than N. In one embodiment, the fertilizer has a nitrogen content between 10-20 wt %.

In one embodiment, the fertilizer contains a growing media. Growing media of the present invention may include, but is not limited to, soil, sand compost, peat, rice hulls, coir, cocopeat, soilless growing media containing organic and/or inorganic ingredients, artificial plant-growth substrates, polymer-based growth matrices, hydrophonic nutrient and growth solutions, organic soil amendments, water, and mixtures thereof.

The fertilizer may include a carrier selected from the group consisting of water, aqueous solutions, slurries, and powders.

Alternatively, the fertilizer may include an additive such as, but not limited to, insecticide, fungicide, nematicide, additional organic fertilizer, bioinsecticide, biofungicide, bionematicide, agricultural or horticultural adjuvants, stickers, spreaders, surfactants, dispersants, humectants, UV protectants, and mixtures thereof. The fertilizer can also contain a source of organic carbon such as, but not limited to, compost and biochar.

Another aspect of the present invention relates to a fertilizer that includes at least one microbe selected from a keratin degrading microorganism and a keratin substrate which is acted upon by the at least one microbe to release nitrogen.

The methods of the present aspect are carried out in accordance with the previous aspect.

In one embodiment, the fertilizer includes at least one microbe selected from the group consisting of *Trichoderma viride* (NRRL B-50520), *Scopulariopsis brevicaulis* (NRRL B-50521), *Scopulariopsis brevicaulis* (NRRL B-50522), and combinations thereof.

Keratin degrading microorganisms of the present aspect can include microorganisms of the genus *Streptomyces*, including but not limited to, *Streptomyces avermitilis, Streptomyces coelicolor*, and *Streptomyces violaceoruber*.

This aspect of the present invention can be carried out using any of the additives and any modes of application described above on any of the above noted plants.

Another aspect of the present invention relates to a method of enhancing growth of plants. The method includes providing a fertilizer comprising at least one microbe selected from the group consisting of *Trichoderma viride* (NRRL B-50520), *Scopulariopsis brevicaulis* (NRRL B-50521), *Scopulariopsis brevicaulis* (NRRL B-50522) and combinations thereof and a substrate which is acted upon by the at least one microbe to release nitrogen. The method further includes contacting the fertilizer with plants or plant seeds under conditions effective to enhance the growth of the plants or plant seeds compared to plants or plant seeds to which the fertilizer was not applied.

The methods of the present aspect are carried out in accordance with the previous aspect.

In one embodiment of the present aspect of the invention, the fertilizer contains gelatin which makes up 5-20 wt % of the granule or pellet.

In practicing all aspects of the present invention, the fertilizer may be prepared in a formulation containing organic or inorganic materials that aid in the delivery or contacting of the organism to the recipient plant or plant seed. Furthermore, in all aspects of the present invention described herein, contacting of the fertilizer with plants or plant seeds, or other plant material, may be carried out either simultaneously with, before, or after the introduction of the plant, plant seed, or other plant propagative material into a growing media or area. The plant, plant seed, or other plant material can be established (propagated) in any suitable planting media, as described supra, without limitation, as well as in any suitable environment, for example, a greenhouse or field environment. A person of skill in the art would readily be able to establish the requirements suitable for sustaining and/or propagating a plant.

Regardless of the order in which contacting the organism to plant, seed, or other plant material is carried out, the following are all suitable methods in accord with the present invention for bringing the fertilizer and plant material of choice in contact. Non limiting examples of these methods include broadcast application, drop application, rotary application, liquid or dry in-furrow application, direct incorporation into soils or greenhouse planting mixes, spray application, irrigation, injection, dusting, pelleting, or coating of the plant or the plant seed or the planting medium with the fertilizer. It also is possible to produce a granular formulation suitable for drop or broadcast spreading, a powdered formulation for addition to potting mixes or directly in field applications, or a liquid fertilizer using the systems described herein.

The fertilizer of the present invention may be applied in the same manner as conventional fertilizers. As known to those skilled in the relevant art, many methods and appliances may be used. In one embodiment, a mixture of microbes of the present invention and substrate are applied directly to soil or plants. In another embodiment, dried powders of the microbes of the present invention and substrate are applied to soil or plants. The fertilizer may be applied to soil, by spreaders, sprayers, and other mechanized means which may be automated. The fertilizer may be applied directly to plants, for example, by soaking seeds and/or roots, or spraying onto leaves. Such application may be made periodically, such as once per year, or per growing season, or more frequently as desired. Although not necessary, the fertilizer of the invention can also be used in conjunction or in rotation with other types of fertilizers.

Beneficial microbes may be formulated or mixed to prepare granules, dusts, or liquid suspensions. These can be mixed directly into soils or planting mixes. The preparations are then mixed into the soil or planting mix volume for greenhouse applications or into the upper volume of field soil (Harman, G, "The Myths and Dogmas of Biocontrol. Changes in Perceptions Based on Research with *Trichoderma harzianum* T-22," *Plant Disease* 84:377-393 (2000), which is hereby incorporated by reference in its entirety). Equipment and procedures for such contacting are well known and used in various agricultural industries. Typical rates are 0.2 to 10 kg of product containing $10^7$ to $10^9$ colony forming units (cfu) per cubic meter of planting mix or soil.

Contacting can also be done by liquid application (drenches) for greenhouse or nursery soils and soil mixes. Liquid suspensions of the beneficial microorganisms can be prepared by mixing dry powder formulations into water or another carrier, including fertilizer solutions, or by diluting a liquid formulation containing the organism in water or other aqueous solutions, including those containing fertilizers. In either case, the formulation may include other organic or non-organic additives to aid in dissolving or applying the mixture. Solutions can then be used to water planting mixes either prior to planting or else when plants are actively growing, such as by field irrigation. Typically, 10 to 400 ml of product (usually 150/inn or smaller in particle size) containing $10^7$ to $10^9$ cfu are mixed with 100 L of water for such applications.

Seeds are commonly treated using slurry, film-coating or pelleting by processes well known in the trade (Harman et al., "Factors Affecting *Trichoderma hamatum* Applied to Seeds As a Biocontrol Agent," *Phytopathology* 71:569-572 (1981); Taylor et al., "Concepts and Technologies of Selected Seed Treatments," *Ann. Rev. Phytopathol.* 28:321-339 (1990), both of which are hereby incorporated by reference in their entirety). The microbes of the present invention can effectively be added to any such treatment, provided that the formulations do not contain materials injurious to the beneficial organism. Depending on the organism in question, this may include chemical fungicides. Typically, powder or liquid formulations ($10^7$ to $10^{10}$ cfu/g) of the organism are suspended in aqueous suspensions to give a bioactive level of the organism. The liquid typically contains adhesives and other materials to provide a good level of coverage of the seeds and may also improve its shape for planting or its cosmetic appeal.

Contacting can also be accomplished by dry powders containing beneficial organisms which are applied as a dust to roots, bulbs, or seeds. Generally, fine powders (usually 250/in or smaller) are dusted onto seeds, bulbs or roots to the maximum carrying powder (i.e., until no more powder will adhere to the treated surface). Such powders typically contain $10^7$ to $10^9$ cfu/g.

Liquid suspensions of the beneficial microorganisms can be prepared by mixing dry power formulations into water or other aqueous carriers, including fertilizer solutions, or by diluting a liquid formulation containing the microbe in water or other aqueous solutions. Such solutions can then be used to water planting mixes either prior to planting or else when plants are actively growing. Liquid suspensions of products may be injected under pressure into the root zone of appropriate plants through a hollow tube located at the depth desired by the application. Equipment for such application is well known in the horticulture industry. Alternatively, suspensions or powders containing appropriate organisms can be applied into wells or other aqueous environments in the soil. Liquid suspensions of products may be prepared as described above for preparing drenches. Such materials may be added to the furrow into which seeds are planted or small plants are transplanted. Equipment for such applications is widely used in the agricultural industry. Typical rates of application are 0.5 to 10 kg of product ($10^7$ to $10^9$ cfu/g) per hectare of field.

Granules can be broadcast onto soil surfaces that contain growing plants, to soil at time of planting, or onto soils into which seeds or plants will be planted. Typical rates of application range from 1 to 500 kg of product containing $10^7$ to $10^9$ cfu/g depending on the plants to be treated and the goals of the treatment. Alternatively, spray solutions can be prepared and applied to give similar rates (Harman, G. E., "The Dogmas and Myths of Biocontrol. Changes in Perceptions Based on Research with *Trichoderma harzianum* T-22," *Plant Dis.* 80:736-741 (1996); Lo et al, "Biological Control of Turfgrass Diseases with a Rhizosphere Competent Strain of *Trichoderma harzianum*," *Plant Disease* 80:736-741 (1996); Lo et al., "Improved Biocontrol Efficacy of *Trichoderma harzianum* 1295-22 for Foliar Phases of Turf Diseases by Use of Spray Applications," *Plant Dis.* 81:1132-1138 (1997), which are hereby incorporated by reference in their entirety).

For the purposes of the present invention, all methods which describe application are designed to accomplish the same purpose, i.e., to provide a means of application that will result in effective colonization of the root by the beneficial organism (Harman et al., "Potential and Existing Uses of *Trichoderma* and *Gliocladium* For Plant Disease Control and Plant Growth Enhancement," In *Trichoderma* and *Gliocladium*, Harman et al., eds., Vol. 2, London: Taylor and Francis (1998), which is hereby incorporated by reference in its entirety).

The present invention can be used to treat a wide variety of plants of their seeds. As used herein, the fertilizer of the present invention supports or enhances plant growth, if in the presence of the fertilizer in the soil, or applied to the roots, stems, leaves or other parts of the plant, the plant or a part of the plant gains viability, size, weight, rate of germination, rate of growth, or rate of maturation. Thus, the fertilizer has utility in any kind of agricultural, horticultural, and forestry practice. The fertilizer can be used for large scale commercial farming, in open fields or in greenhouse, or even in interiors for decorative plants. Preferably, the fertilizer is used to enhance the growth of crop plants, such as, but not limited to, cereal crops, vegetable crops, fruit crops, flower crops, and grass crops. For example, the fertilizer compositions may be used with dicots and monocots. More particularly, plants treated in accordance with the present invention include any plant susceptible to fungal or plant pathogen. For example, plants treated in accordance with the present invention include, but are not limited to, agronomic row or other field crops that include buckwheat, beans (soybean, snap, dry), corn (grain, seed, sweet corn, silage, popcorn, high oil), cotton, canola, peas (dry, succulent), peanuts, safflower, and sunflower; alfalfa hay and forage crops that include alfalfa, clover, vetch, and trefoil; berries and small fruits that include blackberries, blueberries, currants, elderberries, gooseberries, huckleberries, loganberries, raspberries, strawberries, grapes, bulb crops: garlic, leeks, onions, shallots, and ornamental bulbs; citrus fruits that include citrus hybrids, grapefruit, kumquat, limes, oranges, and pummelos; cucurbit vegetables that include cucumbers, melons, gourds, pumpkins, squash, and flowers; bedding plants and ornamentals; fruiting vegetables that include eggplant, sweet and hot peppers, tomatillos, tomatoes, herbs, spices, and mints; hydroponic crops that include cucumbers, tomatoes, and lettuce; herbs and spices; leafy vegetables and cole crops that include arugula, celery, chervil, endive, fennel, lettuce (head and leaf), parsley, radicchio, rhubarb, spinach, Swiss chard, broccoli, Brussels sprouts, cabbage, cauliflower, collards, kale, kohlrabi, mustard greens, and asparagus; legume vegetable and field crops that include snap and dry beans, lentils, succulent and dry peas, peanuts, and soybeans; pome fruit that include pears and quince; crops that include beets, sugarbeets, red beets, carrots, celeriac, chicory, horseradish, parsnip, radish rutabaga, salsify, turnips; shadehouse and other nursery crops that include deciduous trees (maple, oak), ornamentals, grapes, citrus, pine; small grains that include rye, wheat, sorghum, and millet; stone fruits that include apricots, cherries, nectarines, peaches, plums, prunes, tree nuts: almonds, beech nuts, Brazil nuts, butternuts, cashews, chestnuts, filberts, hickory nuts, macadamia nuts, pecans, pistachios, and walnuts; tuber crops that include potatoes, sweet potatoes, yams, artichoke, cassava, and ginger. Other examples include those grasses associated with turfgrass, turf, sports fields, parks, established and new preparation of golf course tees, greens, fairways and roughs, seed production and sod production. Plants that may be treated also include petunia, pelargonium, poinsettia, chrysanthemum, carnation, and zinnia.

Plant growth enhancement of the present invention may be in the form of greater root mass, greater depth of rooting, greater shoot mass, greater length of shoots, increased leaf greenness, increased yields, and improved stand and vigor. Plant growth can be established and ascertained by other means besides the extrinsic properties listed above. A person of skill in the art would readily be able to establish physical, biochemical or genetic assays to identify and/or quantify plant growth or viability.

Plants derive numerous advantages from root colonization by the fertilizer disclosed herein. One advantage is protection of plants against diseases by direct action of the microbe strains on pathogenic microbes (see Chet, L, "*Trichoderma*—Application, Mode of Action, and Potential as a Biocontrol Agent of Soilborne Plant Pathogenic Fungi," In Innovative Approaches to Plant Disease Control, pp. 137-160, 1. Chet, ed., J. Wiley and Sons: New York (1987), which is hereby incorporated by reference in its entirety) or other deleterious soil microflora (Bakker et al, "Microbial Cyanide Production in the Rhizosphere in Relation to Potato Yield Reduction and *Pseudomonas* spp-Mediated Plant Growth-Stimulation," *Soil Biol. Bio-Chem.* 19:451-457 (1987), which is hereby incorporated by reference in its entirety). Microbes offer protection against plant pathogens due to systemic induction of resistance. This permits plants to be protected at a point widely separated (temporally or spatially) from application of microbes (see Harman et al., "*Trichoderma* Species—Opportunistic, Avirulent Plant Symbionts," *Nature Microbiol. Rev.* 2:43-56, (2004), which is hereby incorporated by reference in its entirety). For example, through induced resistance, the microbes disclosed herein can control foliar pathogens even when it is present only on the roots.

Another advantage is that the fertilizer of the present invention can provide protection against abiotic stress due to drought (water deficit), disease or other unfavorable plant growth conditions. Often times, plants may be cultivated in climates where the crop is exposed to many biotic and abiotic stresses such as plant diseases and drought. Drought conditions affect gene expression, amino acid profiles, and photosynthesis in plants thereby inducing stress. The majority of these responses may be delayed in plants treated with the fertilizer of the present invention. It may be possible to improve the tolerance of plants to drought by treating plants with microbes of the present invention in the field. Plants with improved tolerance to drought, disease, and stress would be of benefit to the farmers by stabilizing crop yields and profitability.

The microbes used in the fertilizer disclosed in the present invention may result in more and deeper roots and reduce the nitrogen requirement for plant growth presumably by enhancing nitrogen uptake. This capability can also be used to reduce nitrogen requirements for plant producers. These strains can also increase tolerance of plants to drought.

To understand the relevance of the present invention, a consideration of the plant yield plateau is of importance. Plants generally respond to increasing nitrogen fertilizer levels with increased yield and growth up to a point and then the yield increase levels off; this is the yield plateau above which use of nitrogen fertilizer no longer increases yields. Planting seeds treated with the microbes (i.e., *Trichoderma viride* (NRRL B-50520), *Scopulariopsis brevicaulis* (NRRL B-50521), and *Scopulariopsis brevicaulis* (NRRL B-50522)) of the present invention have been shown to increase plant growth and productivity even under conditions of substantial nitrogen deficiency (see Harman, G., "Myths and Dogmas of Biocontrol. Changes in Perceptions Derived from Research on *Trichoderma harzianum* T-22," *Plant Dis.* 84:377-393 (2000); Harman et al, "Enhancing Crop Performance and Pest Resistance with Genes from Biocontrol Fungi," In M. Vurro, J. Gressel, T. Butt, G. E. Harman, A. Pilgeram, R. J. St. Ledger and D. L. Nuss (eds.), Enhancing Biocontrol Agents and Handling Risks pp. 114-125. IOS Press, Amsterdam (2001); Harman et al., "*Trichoderma* Species—Opportunistic, Avirulent Plant Symbionts," *Nature Rev. Microbiol.* 2:43-56 (2004), which are hereby incorporated by reference in their entirety). Plants grown in the presence of the symbiotic biocontrol fungus frequently are greener and more vigorous (Harman, G., "Myths and Dogmas of Biocontrol. Changes in Perceptions Derived from Research on *Trichoderma harzianum* T-22," *Plant Dis.* 84:377-393 (2000), which is hereby incorporated by reference in its entirety). Previous research has found that in the presence of *T. harzianum*, yield plateaus were reached with 40-50% less nitrogen fertilizer than in its absence (Harman et al., "Enhancing Crop Performance and Pest Resistance with Genes from Biocontrol Fungi," In M. Vurro, J. Gressel, T. Butt, G. E. Harman, A. Pilgeram, R. J. St. Ledger and D. L. Nuss (eds.), Enhancing Biocontrol Agents and Handling Risks pp. 114-125. IOS Press, Amsterdam (2001), which are hereby incorporated by reference in their entirety). This means that nitrogen fertilizer rates could be reduced by this amount without a yield decrease. This has great potential both for decreasing evolution of $N_2O$ from soils, since less total fertilizer is applied, and since a greater percentage of the applied nitrogen must be taken up by the plant, the requirement for nitrogen in plant metabolism is not expected to be altered, and, therefore, the only way to obtain the added N in the plant is via enhanced N use efficiency.

Another aspect of the present invention relates to a method of making a fertilizer comprising amino acids and ammonia. This method includes providing at least one microbe selected from the group consisting of *Trichoderma viride* (NRRL B-50520), *Scopulariopsis brevicaulis* (NRRL B-50521), *Scopulariopsis brevicaulis* (NRRL B-50522), and combinations thereof and providing a substrate which is acted upon by the at least one microbe to release nitrogen. The method further includes contacting the at least one microbe and the substrate under conditions effective to cause the at least one microbe to act on the substrate and produce a liquid suspension comprising amino acids and ammonia.

This aspect of the present invention can be carried out using any of the additives and any modes of application described above on any of the above noted plants.

In this aspect of the present aspect, the fertilizer may be in a liquefied form of all or a part of the substrate (i.e., keratin) as a result of fermentation. Such fermentation will produce amino acids, peptides, and/or ammonia.

Another aspect of the present invention relates to an isolated *Trichoderma viride* strain deposited with Agricultural Research Service Culture Collection under number NRRL B-50520. The isolated *Trichoderma viride* strain may be in a biologically pure form.

Another aspect of the present invention relates to an isolated *Scopulariopsis brevicaulis* strain deposited with Agricultural Research Service Culture Collection under number NRRL B-50521. The isolated *Scopulariopsis brevicaulis* strain may be in a biologically pure form.

Another aspect of the present invention relates to an isolated *Scopulariopsis brevicaulis* strain deposited with Agricultural Research Service Culture Collection under number NRRL B-50522. The isolated *Scopulariopsis brevicaulis* strain may be in a biologically pure form.

EXAMPLES

The following examples are provided to illustrate embodiments of the present invention but are by no means intended to limit its scope.

Example 1

Isolation of Effective Microorganisms that Degrade Waste Proteins

One of the most widespread proteins present in agricultural wastes is keratin. This is the structural component of hair, feathers and other similar substances. While keratin is generally degraded slowly in soil or elsewhere, there are microbes that degrade this substrate relatively rapidly.

The organisms of the present invention can be grown in liquid fermentation and ammonia and amino acids will be released. For use with the NRRL strains described herein, an additional nutrient may be used, such as tripticase soy broth (Difco Products). Feather meal at 1 to 10% w/v is added to the tripticase soy broth in water and the mixture is sterilized by autoclaving. When the organisms are added to this sterile medium, feather meal is degraded. The release of ammonia from feather meal creates an alkaline environment. Since ammonia at a high pH is strongly volatile, the presence of this material is easily detected by smell. Systems for harvesting and continuous removal of the ammonia are readily available and known to those skilled in the art. One method is simply to have a closed sterile closed loop outside the fermentation vessel that includes a sterile air sparging device. As air is introduced through the fermentation liquid, ammonia will be removed and can be trapped by passage into an acidic solution, vinegar would be satisfactory. This will result in the formation of ammonium acetate, which can be readily used as a fertilizer, and this sparging step will result in concentration of the ammonia for further use. If it is desired also to remove the amino acids, this step can be accomplished by passage of the fermentation liquid through an appropriate ion exchange resin, from which the amino acids can be eluted and thereby concentrated. At the same time, this sparging process will remove the excess ammonia that drives up the pH and thereby allow the fermentation to continue. This can be developed into a continuous flow system for efficient production ammonia.

The present invention sought to determine effective microbes that degrade proteins. To accomplish this, feather meal was mixed with peat moss and moistened the mixture (composition: 1 L peat moss, 1 L feather meal and 400 ml of water), autoclaved the mixture on two successive days, and inoculated the mixture with 1 g composted chicken manure. The peat moss was used as bulking/aeration component and the composted chicken manure was considered a good source of keratin (i.e., feather)-degrading microorganisms. Within six days of inoculation, a strong odor of ammonia was present, indicating degradation of the feathers to ammonia, which is an excellent natural nutrient for plants. The organisms present in the ammonia-scented media were plated using dilution techniques on both potato dextrose agar ("PDA") ("Difco") and on tripticase soy agar ("TSA") ("Difco") made up according to the manufacturer's directions. Microbial growth on the PDA, which is a general mycological medium, was generally poor, but on TSA, which is a hydrolyzed soy protein, numerous fungi grew. These, surprisingly, consisted of only three different microorganisms that apparently were able to grow well on feather meal while most other of the abundant microbes that occur in compost could not. These fungi were isolated, obtained in pure form by single sporing and stored on silica gel at −20° C., which is a very good way of preserving fungi.

The fungi isolated from the chicken manure compost were inoculated into tripticase soy broth ("TSB") and grown for three days. Good growth of all microorganisms was obtained in the TSB and 50 ml of the actively growing cultures was added to the feather meal:peat mixture contained in sterilized plastic boxes with flanged lids that provide good aeration of the contents of the boxes. After six days of growth, samples were removed and extracted and the levels of soluble nitrogen compounds were determined. The extracts were analyzed for amino acids (ninhydrin assay) or ammonia (Nessler's reagent; LaMotte Testing kit).

Promising results were obtained with the fungi obtained. The ammonia level, with lysine as the standard, for the control sample was about 19 µg/ml, while the values were 600, 3240, and 4900 µg/g, respectively for the three strains. The amino acid levels for the same samples were 2800, 3003, and 5600 µg/g for the same three strains, while the control values were about 3 µg/ml. These assays were repeated several times with similar results. Several strains in particular degraded keratin more efficiently than any other tested microbes.

Example 2

Identification of the Keratin-Degrading Fungi and Bacteria

The fungi identified in Example 1, supra, were sent to the USDA type culture collection for deposit in their patent collection. The strains were designated as NRRL B-50520, NRRL B-50521, and NRRL B-50522 for the green-, brown-, and white-spored strains, respectively. These fungi were identified as *Trichoderma viride* (NRRL B-50520), and *Scopulariopsis brevicaulis* (NRRL B-50521 and NRRL B-50522 are both isolates of this fungi). Both species have penicillate conidiophores, but subtle differences in the arrangements of the conidiophores clearly place them in their respective genera. The ITS regions of each of the isolates were also sequenced and assessed by GenBank BLAST queries. As a result, their identity is confirmed as follows:

NRRL B-50520—*Trichoderma viride*
NRRL B-50521—*Scopulariopsis brevicaulis*
NRRL B-50522—*Scopulariopsis brevicaulis*

*Trichoderma viride* has a very low risk profile. The US Environmental Protection Agency states, relative to use of a strain within this genus as a biocontrol agent against fungal pathogens, "the Agency anticipates that no additional health effects data are required for the currently registered sites for *Trichoderma polysporum* and *T. viride*" (*Trichoderma* species Summary Document, Registration Review: Initial Docket, Unites States Environmental Protection Agency (April 2007), which is hereby incorporated by reference in its entirety). The same is true for most other fungi in the genus *Trichoderma*.

A recent review lists organisms that produce keratinases (Brandelli et al., "Biochemical Features of Microbial Keratinases and Their Production and Applications," *Applied Microbiology and Biotechnology* 85:1735-1750 (2010), which is hereby incorporated by reference in its entirety). *S. brevacaulis* is described as a producer of keratinase, but *T. viride* is not. However, there is a single report of production of keritanase by a strain of *T. viride* from India (Jyoti et al., "Keratinolytic Enzymes From *Trichoderma viride* and *Graphium cuneiferum* Isolated From Poultry Farms at Jabalpur, India," *Cryptogamic Botany* 4:30-33 (1993), which is hereby incorporated by reference in its entirety).

Example 3

Methods of Production of Useful Formulations

Feather meal is a coarse brown powder. Dry fertilizers for use in many applications need to be applied as granules through drop or rotary dispersal systems. Therefore, a method was developed for making a useful granule. A method for solidifying and production of granules with dimensions of 2-5 mm in diameter was required. The initial granule was prepared by adding sufficient water to the feather powder to produce a slurry and then dissolving in this slurry gelatin to a final concentration of about 7% relative to feather powder. This material was spread in a sheet and dried and the result was a hard brown sheet. This was then ground and sieved to provide particles of the desired size. It will be appreciated that a similar composition can be extruded and dried to give appropriately sized particles. Similarly, these mixtures can also be used in pelleting equipment, followed by appropriate sizing.

The granules thus produced do not contain any added microorganisms. Some systems for producing granules or pellets involve heat and pressure, so a coating procedure was developed for the pellets. Conidia of the *Trichoderma* strains known to provide benefits, including enhanced nitrogen use efficiency were added to 0.1% Crystal Tex (tapioca dextran, National Starch) to give about $10^5$ colony forming units per ml of suspension. This mixture was applied to the surface of the dried pellets to give a smooth and continuous coat that did not appreciably increase the size of the granules. Thus, the living fungi were applied as a dry coating. From this location, they grew immediately when the pellet was moistened (FIG. 1).

In later experiments, direct addition of the strains to the mix while moist and before it was extruded to form the pellets was examined. This method works very well and the organisms remain stable so long as drying temperatures remained at or below 38° C. Selection of the appropriate microorganisms (i.e., microbes) is helpful in obtaining the best results. These microbes serve two functions: (1) some microbes have the ability to degrade feather meal or other recalcitrant proteins, and (2) some microbes act as endophytic plant symbionts. In the experiments of the present invention, in the absence of microbes, N, as judged by turf plant greenup only occurs 4-6 weeks after application. By this time, in the presence of the degrading microbes, most of the N is already released. The endophytic plant microorganisms have many functions, one of which is increased plant nitrogen use efficiency ("NUE"). If this microbial component is included, then the effective N value of the fertilizer is increased. Thus, the amount of N in a 14% N fertilizer effectively becomes 28% when the NUE contribution is included. This is a useful aspect of the present invention if this invention is to be competitive with, and as effective, as standard synthetic fertilizer with 30% N. Plants still require the same level of N to grow and thrive, so the only way that a fertilizer in the present invention becomes as effective at the same application rate (useful for economic competitiveness) is through the use of NUE enhancing organisms.

Standard synthetic fertilizers contain high levels of salts, and the osmotic potential and direct effects of these components is lethal to microbes. However, in this invention, synthetic salts are almost completely eliminated, and thus, a granule containing a microbe is safe for the microbe. Most of the granule is protein, which is not toxic to the microbes. Thus, either the coating or direct mixing of the microbial agents is one component of this invention.

The microbial component and the nonliving components can be formulated into a single granule or other mixture. There are many cases in the literature where, for example, microbes added to or living in the soil increase plant growth including NUE. However, users will be unwilling to apply a number of different organisms and other products to accomplish a valuable result. The inclusion of all the living and nonliving components into a single product or granule is one component of this invention.

This embodiment of the invention provides a granule composed almost entirely of protein. Proteins are 12-14% N, so since gelatin and feather meal are both animal proteins the necessary value is obtained.

For some applications, a granular product is not necessary for some applications. Powders are frequently used, for example as components of plant growth media and as materials to be added directly to fields or gardens, typical nitrogen values for a granule such as this is 12-14%. Admixtures of feather meal and microorganisms described herein can be used directly.

In addition, any number of additions can be made to this basic granule or powder. An example is the liquid ammonia and amino acid mixture extracted from the growth medium as in Example 2, supra. This can be used directly in the dry powder or granule or concentrated to give an even higher level of N. Since feather powder or gelatin will provide very little immediately available N, such additions are useful for providing immediate green up. Other suitable nitrogen sources are fish meals or extracts, compost extracts, kelp extracts, extracts of sea animals such as shrimp or shellfish. Inorganic sources include nitrates, inorganic ammonia sources and the like. In addition, organically-listed products such as K from greensand or organically listed potassium sulfate, and other sources of K that are not listed can be added. Similarly, P can be supplied as bone meal (organic) or from various inorganic salts. For lawn applications, P is being banned and a component of use of feather meal or gelatin is that P is not present.

Example 4

Fertilizer for Grass

A very demanding use of fertilizers is for application to grass in lawns, sports arenas, parks, golf courses and other similar uses. The fertilizers must provide a highly attractive surface and last for a considerable period of time. The granule was prepared to contain 73.8% feather meal, 13% Chilean nitrate, 7.3% gelatin, and 5.7% Jersey green sand (source of K). The Chilean nitrate is currently organically certified and contains 16% N, so its nitrogen content is just a bit above that of the protein components. As a comparison, the preparations that were produced were tested against Scotts® Turf Builder®, a widely used home fertilizer which has an analysis of 30:2:8 N:P:K (as N, $P_2O_5$ and $K_2O$). By comparison, it was anticipated that the analysis of the fertilizer that was prepared would 15-16:0:0.3, so it would not be a complete fertilizer. P was not included, since this is not allowed in many jurisdictions because of the danger of pollution of P into water which results in eutrophication. The N level was less than 50% as high as that of the Scotts® fertilizer, and the K level is suboptimal. Thus, if the performance of the fertilizer preparations of the present invention approaches that of Scotts®, it demonstrates that (a) a significant amount of N is being released from the fertilizer, (b) there is increased efficacy of uptake of N induced in the turf plants by the fungi added, and (c) there is much less availability of N to leach into groundwater. After all, plants still need the same amount of N to grow and, if only half as much nitrogen is being added, there must be greater uptake of N and there can be only small amounts of N that leach into groundwater.

The tests were conducted in an annual rye grass planted into a 1:1 sandy loam:peat mix that contains almost no free nitrogen. Annual rye grass was planted in flats and after seedlings were well established, about two weeks after planting, the various fertilizers were applied. Granules were applied at the 1× rate, which is the level of fertilizer applied at the recommended rate for Scotts® Turf Builder®. In addition, every treatment was applied at two times this rate. The first experiments contained a number of treatments as follows:

No treatment control
Granules applied without any microorganisms
Granules applied with B-50520
Granules coated with B-50521
Granules coated with B-50522
Granules applied with B-50520+*Trichoderma* strains K1-K4 (described in the next example)
Granules coated with B-50521+*Trichoderma* strains K1-K4
Granules coated with B-50522+*Trichoderma* strains K1-K4.
Scotts® Turf Builder® fertilizer All were applied at the 1× and 2× rate. In this example, K1-K4 consisted of the following strains: *T. harzianum* strain RR17Bc (ATCC accession PTA 9708); *T. harzianum* F11Bab (ATCC accession PTA 9709), *T. atroviride* strain WW10TC4 (ATCC PTA accession 9707) and *T. virens* strain 41 (ATCC accession 20476).

The results of these trials were successful and are summarized in FIGS. 2A-2B and FIGS. 3A-3D.

Figure 2A:
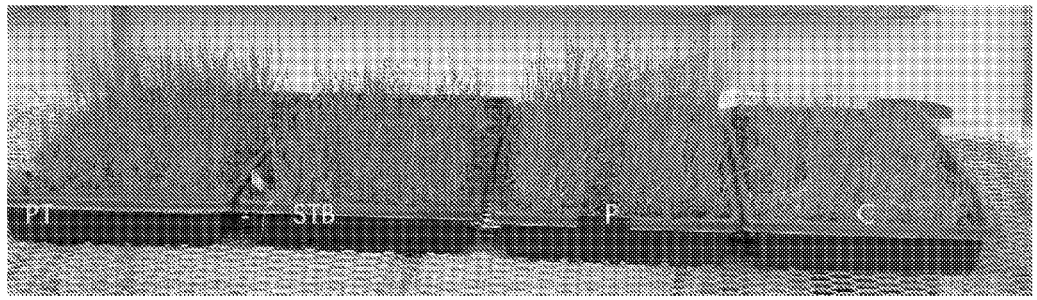
FIGS. 2A-2B illustrate fertilizer comparisons using preparations described in the present invention or commercially obtained.
Figure 2B:

In FIG. 2A, the treatments used were PT (organic fertilizer, NRRL B-50521, and K1-K4, which included *T. harzianum* strain RR17Bc (ATCC accession PTA 9708), *T. harzianum* F11Bab (ATCC accession PTA 9709), *T. atroviride* strain WW10TC4 (ATCC PTA accession 9707), and *T. virens* strain 41 (ATCC accession 20476)); STB=Scotts® Turf Builder®; P=organic fertilizer with NRRL B-50521; and C=untreated control. In FIG. 2B, the treatments used were PT (organic fertilizer and NRRL B-50521); OFC=organic fertilizer granules without any fungi; P (organic fertilizer with NRRL B-50521). FIGS. 2A-2B show growth about 10 days after fertilization by scattering the granules across the surface of the soil in which the grass was growing. Increases in growth are primarily a function of available soluble nitrogen. As can be seen, the growth of grass was substantially greater with the organic fertilizer in the presence of NRRL B-50521 than with any treatment without this organism. Comparable results were seen using NRRL B-50520 or NRRL B-50522. Growth of the grass was also greater than with the commercial lawn fertilizer at this time period. The organic fertilizer control also grew better than the control with no granules; in part this can be attributed to the small amount of organic Chilean nitrate (NaNO$_3$ primarily) that was added to the granules as a starter fertilizer. This illustrates the utility of the invention disclosed here, which includes microbially-mediated slow release nitrogen.

FIGS. 3A-3D contain graphs showing growth over time. To obtain this data, grass was clipped from the flats, dried, and weighed to simulate a mowing event (in FIGS. 2A-2B, the grass was ready for cutting) and this was continued over the course of the experiment. All of the cuttings were done the same day, so the graphs represent the amount of grass that was harvested between the last cutting and the next and days after harvest represents the day after fertilization at which the cutting was made.

Figures 3A, 3B, 3C, 3D:
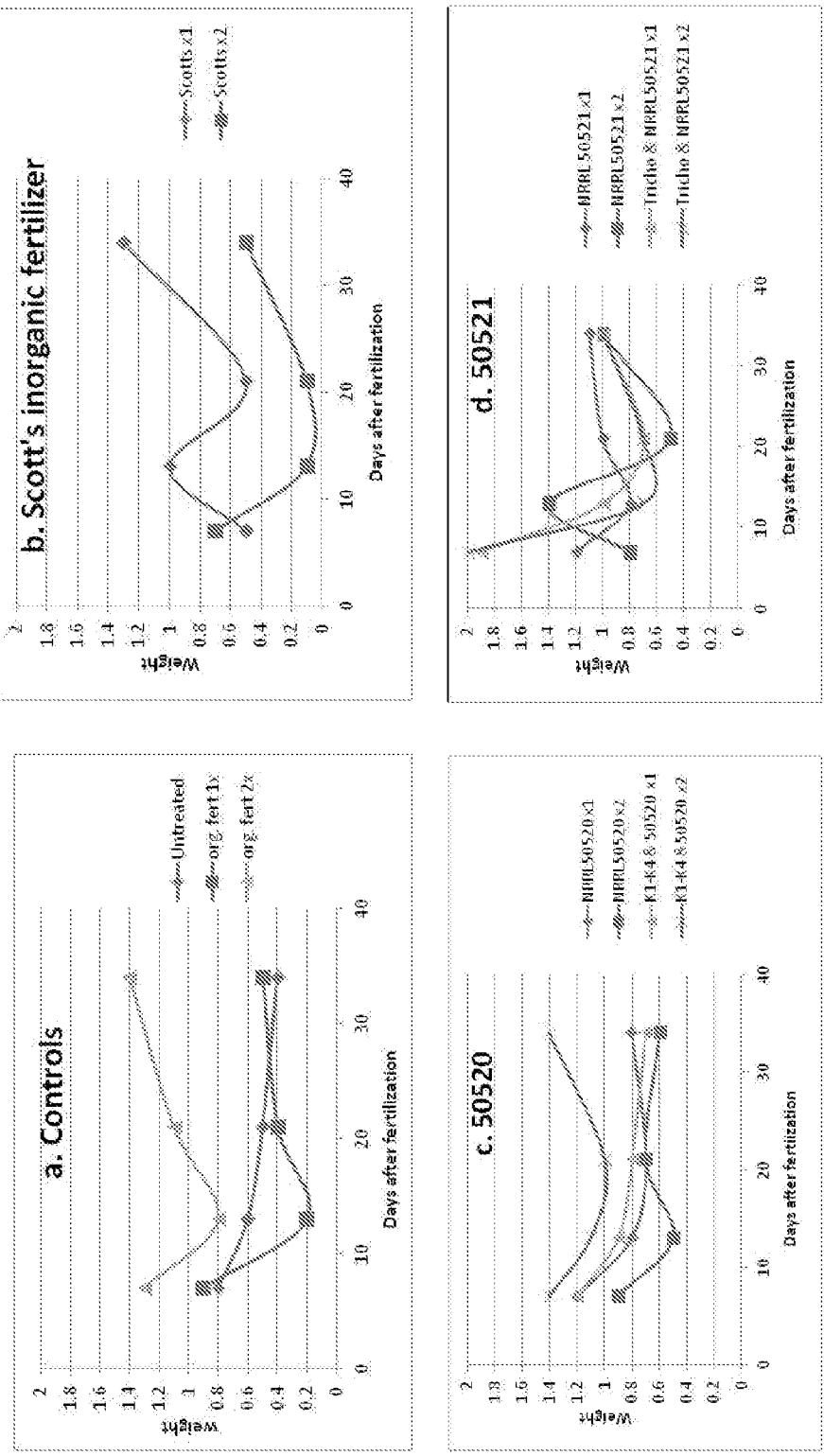
FIGS. 3A-3D show harvest weights of grass over time using different fertilizer treatments.

The untreated grass had, at its highest level of cuttings, 800 mg/flat at 7 days after planting, and thereafter the cutting weights declined to very low levels (FIG. 3A). The organic fertilizer at the 1× rate was similar to the untreated control, but at the 2× rate, the weights were substantially larger. The organic fertilizer at the first cutting was high, which no doubt represents the nitrogen supplied by the Chilean nitrate that was provided in the granule. After another week, the grass weights dropped and then increased again (FIG. 3A). This second increase is no doubt due to hydrolysis of the feather meal by the native soil microflora.

The standard, Scotts® Turf Builder®, initially supported modest growth at the 1× level, but this increased at the second cutting. Growth decreased again at the third cutting and increased again finally at the last cutting (FIG. 3B). This likely reflects changes in availability of different nitrogen sources. However, at double time rate, grass yields were extremely low at the second and third cutting times (FIG. 3B). This was caused by burning of the grass at this level of application, which never occurred with any of the feather meal based systems.

At the 1× rate, strain NRRL B-50520 gave grass cutting yield results that were substantially better than the control organic fertilizer (FIGS. 3A and 3C). Strain NRRL B-50521 gave rapid release of nitrogen as evidenced by very high grass yields at the first cutting, but then grass yields in most cases declined dramatically by the second cutting. This is due to very high release of soluble nitrogen and then the substrate was depleted.

In these experiments, it should be noted that the Scotts® fertilizer is a relatively complete fertilizer while, as noted earlier, the test materials used contained no phosphorus and inadequate levels of potassium.

Example 5

Pool Sizes of Soluble Nitrogen Compounds in Soil and Grass Fertilized with Different Materials It is indicated in the above examples that the fertilizer prepared by other methods will have low levels of leaching of nitrates into ground water. If this is true, then levels of nitrate should be lower than in soils fertilized with standard chemical fertilizers. At the same time, other forms of soluble nitrogen should increase since degradation of feather meal results in release of amino acids and ammonia. These compounds would only be converted to nitrate by activity of soil microflora over time. However, amino acids and ammonia are likely to be rapidly taken up by plants (or microflora) and so pool sizes will not accumulate to large levels. Thus, the amount of free nitrogen in any form is likely to be smaller in soils with the samples of the present invention than with the standard chemical fertilizer. Data from soil sampled nine days after fertilization is given in Table 1 that follows. 1 g of soil was extracted per 3.6 ml of extraction buffer and the colorimetric tests described supra were used to measure the soluble nitrogen in the extracts. For the amino acid levels, data was based on a dilution curve with lysine as the standard. All of these assays were done at the 1× the rate of fertilizer application.

TABLE 1

Amounts of Different Forms of Soluble Nitrogen in Soil

| Treatment | Nitrate (µg/g) | Ammonia (µg/g) | Amino acids (µg/g) |
|---|---|---|---|
| Untreated | >5 | 21 | 43 |
| Scotts ® Turf Builder ® | 75 | 20 | 68 |
| K1-K4 on granules | 5 | 11 | 86 |
| B-50520 on granules | 5 | 15 | 90 |
| B-50521 on granules | 7.5 | 15 | 107 |
| K1-K4 + B-50520 | 5 | 22 | 68 |
| K1-K4 + B-50521 | 5 | 22 | 75 |

The values for nitrate in soil were exactly as predicted. With the chemical standard fertilizer, the level of nitrate is more than an order of magnitude greater than with the untreated control soil of with any of the feather-meal-based granular products. Ammonia levels change little across treatments, probably because any ammonia released is immediately taken up by the turf which was already growing and established. However, the levels of amino acids did change. The greatest level of amino acids was with the granules with NRRL B-50521. This correlates well with the rapid increase in growth of turf early on when fertilized with granules containing this organism (FIG. 3D). Interestingly, the addition of K1-K4 to the granules containing either B-50520 or B-50521 reduced the levels of amino acids. This may be a consequence of the apparent conversion of reduced forms of nitrogen (amino acids or ammonia) to nitrate. If the concept of enhanced turf growth by in vivo hydrolysis of the feather meal is correct, then the pool sizes of nitrogenous compounds in the turf plants themselves ought to change both quantitatively and qualitatively. Table 2 gives the concentrations in plant tissue of nitrate, ammonia and amino acids (as lysine equivalents) that could be extracted from grass seedlings 14 days after planting. In these experiments, grass was dried and then extracted and the levels of the various soluble N forms measured by procedures already described.

TABLE 2

Concentration of Nitrate, Ammonia, and Amino Acids in Plant Tissue

| Treatment | Nitrate (µg/g) | Ammonia (µg/g) | Amino acids (µg/g) |
|---|---|---|---|
| Untreated control | 10 | 936 | 2600 |
| Scotts ® Turf Builder ® | 700 | 962 | 3380 |
| K1-K4 on granules | 15 | 686 | 4212 |
| B-50520 on granules | 15 | 1477 | 3380 |
| B-50521 on granules | 15 | 1352 | 3900 |
| K1-K4 + B-50520 | 150 | 988 | 3224 |
| K1-K4 + B-50521 | 150 | 910 | 3224 |

This data confirms the expectations that the source of nitrogen makes a difference in the forms of soluble nitrogen in plant tissues. It must be emphasized that these values are snap shots of the size of the active nitrogen metabolic pool in plants, and that there is a constant rebalancing between uptake from the environment and metabolism of the nitrogen on to proteins and other nitrogenous compounds in the turf. The untreated control has low levels of all forms of N, which explains the poor growth noted above. With the exception of B-50520 and B-50521 on granules, ammonia levels vary within a small range, but in the case of these two fungi on granules, the levels are considerably higher. The levels of ammonia appeared to be reduced if K1-K4 was added to B-50520 or B-50521. This may be explained by the conversion of ammonia to nitrate by these fungi, as suggested by the increase in nitrate in seedlings grown in the presence of both fungi.

Seedlings grown in the presence of the commercial fertilizer have very high levels of nitrate, again as would be expected. A principal nitrogenous component of this fertilizer is nitrate and this clearly is reflected in the values obtained. High levels of nitrates are pollutants of water, and these data reflect the point that the amount of nitrate saturates the plants' abilities to absorb this nutrient and much of this will end up as water and air pollutants. Seedlings grown in the presence of feather meal granules and microbial mixture K1-K4, and NRRL B-50520 or B-50521, all had only about 2% as much nitrates in their tissue as did those grown in the presence of the inorganic lawn fertilizer. As seen in the previous example, they grew much better than the levels of nitrate in their tissues would predict. However, the pool sizes of amino acids were enhanced, as was the level of ammonia. Amino acids and ammonia are downstream of nitrate in plant assimilation and nitrogen transformation—in plants, nitrate needs to be transformed to ammonia and then on to amino acids before they can become assimilated and converted to a structural or active component of plant metabolism. So, this higher level of readily available N without the energy-expensive step of reduction to ammonia will improve plant growth and nitrogen use efficiency. Also demonstrated is the potential for greatly reduced nitrate pollution of ground and surface water. Surprisingly, the level of nitrate in plants when B-50520 or B-50521 were added together with K1-K4, the level of nitrate in plant tissue increased. This may be because there are interactions between these groups of fungi that result in greater oxidation of amino acids or ammonia to nitrate.

Example 6

Production of BioPreferred Fertilizer Products

As shown in FIG. 1, the formulation of the products used to generate the data in that figure supported growth of grass about as well as Scotts® fertilizer, and at only a slightly elevated application rate for about 5 weeks. However, thereafter, results were less effective, while Scotts® synthetic fertilizer was effective for about 8 weeks.

In addition, it was discovered that the price of feather meal increased 2-3 fold over the summer of 2012, which overpriced products containing it. The answer seemed to be to produce a BioPreferred, rather than a product which could be OMRI certified. As noted earlier, BioPreferred products are required to contain, at a minimum, 71% of the total as organic farm materials. Thus, a synthetic slow release nitrogen source with a high N level could be used. A granule was prepared that contained, on a dry weight basis, 71% organic protein (primarily feather meal), 20% methylene urea (a slow release synthetic nitrogen source), with the remainder divided between potassium sulfate and Chilean nitrate. The N:P:K ratio was about 17:0:9 and the slow release N was expected to provide an extended life of the product. The granules so produced were coated or contained Trichoderma strains K1-K4 plus Trichoderma viride NRRL B-50520 to provide the NUE benefit to make the product perform in a manner equivalent to Scotts® Turf Builder® with 32% N.

In addition, another product was prepared. This one contained 46% organic protein sources, primarily feather meal, and 26% garden compost. It also included methylene urea to a level of 23% of the total and the remainder was composed of Chilean nitrate and potassium sulfate. This product had an N:P:K ratio of 16:0:3 and contained 71% BioPreferred components. This product was expected to have similar capabilities as the one described in the previous paragraph; however, it was expected to be about 20% cheaper because of the reduction in the amount of the organic protein. It is also an advantage to have a greater amount of organic matter in the preparation from the compost.

The granules also can contain nonproteinaceous binders (e.g., gelatin) such as dextrans, starches, polyvinyl chloride or other similar materials.

Figure 4:
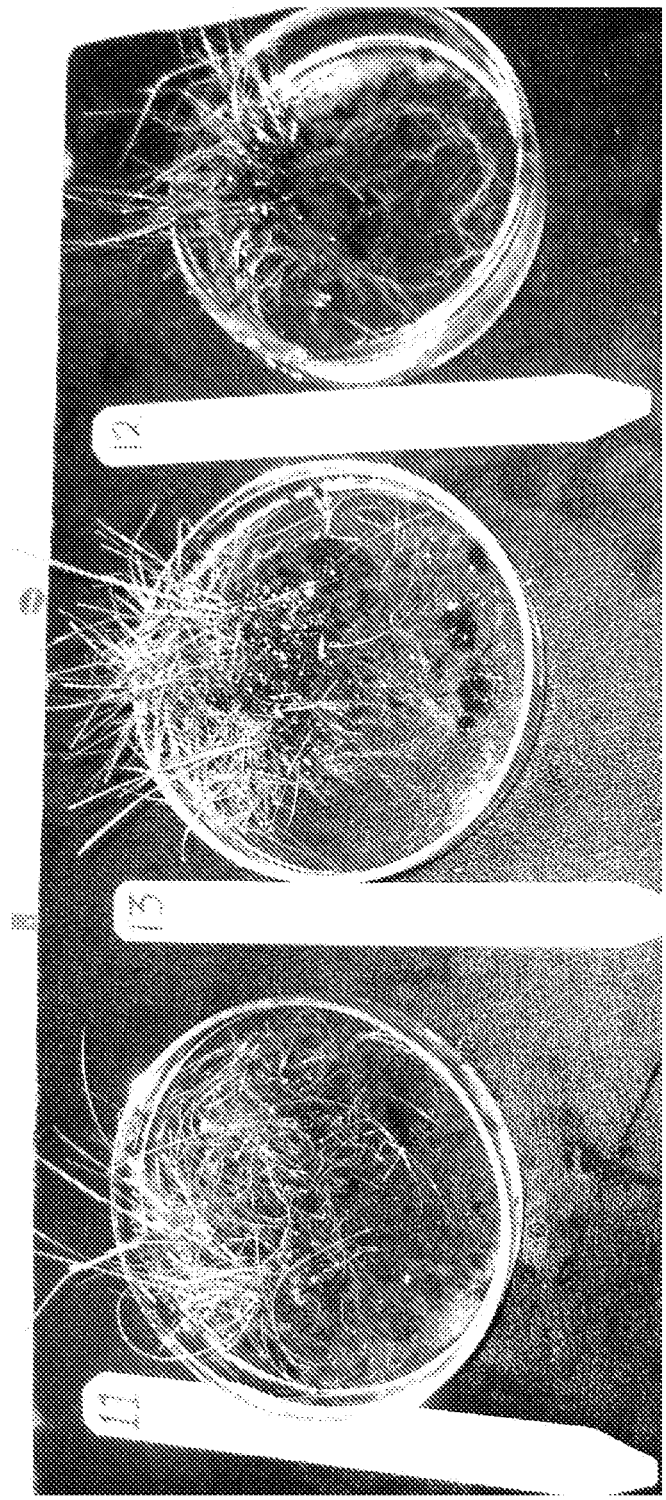
FIG. 4 shows root development of turf grown in a sand:peat mix for about 6 weeks and fertilized with the granules described in this example with and without the beneficial microbial mix *T. virens* stain NRRL B-50521 and *Trichoderma* strains K1-K4 (*T. harzianum* strain RR17Bc, *T. harzianum* F11Bab, *T. atroviride* strain WW10TC4, and *T. virens* strain 41). The petri dish labeled 11 shows root growth on turf fertilized with the granules without the beneficial microbes. The dish labeled 12 contained the organisms incorporated into the granules at about $10^5$ cfu/g, while the dish labeled 13 was fertilized with granules coated with the beneficial fungi in a dextran mixture ($10^5$ colony forming units (cfus)/ml in 2% tapioca dextran to form a thin continuous coat).

Granules produced using the technologies and systems described in this herein perform well in actual tests. However, they provide their best performance when combined (either through coating of granules or internal incorporation, with beneficial microorganisms). FIG. 4 shows one example of this, that of increased turf root development. Strains K1-K4 have been repeatedly shown to increase plant root growth from seed treatments or other methods of application in wheat, maize, tomatoes, and other crops. This attribute of increasing plant root development and deeper colonization of soil is a component of the abilities of K1-K4.

FIG. 4 shows root development of turf grown in a sand:peat mix for about 6 weeks and fertilized with the granules described in this example with and without the beneficial microbial mix T. vixens stain NRRL B-50521 and Trichoderma strains K1-K4. Root growth on turf fertilized with the granules without the beneficial microbes is show in the petri dish labeled 11. The petri dish labeled 12 contained the organisms incorporated into the granules at about $10^5$ cfu/g, while the dish labeled 13 was fertilized with granules coated with the beneficial fungi in a dextran mixture ($10^5$ colony forming units (cfus)/ml in 2% tapioca dextran to form a thin continuous coat). These are variations on the methods of adding beneficial microbes. The greater root growth (turf roots are quite small and fine) are evident in the lower half of the petri dishes with either method of application of the beneficial microbes but absent in the turf fertilized with the granules in the absence of the beneficial microbes.

There are two microbial components to this invention. First, microorganisms that increase degradation of natural recalcitrant sources of N such as feather meal to convert them into simple compounds that can be used for plant nutrition. Second, microorganisms, such as K1-K4 that have the ability to increase plant growth and productivity, including enhancing root growth, NUE, improving resistance to abiotic stresses, and improving plant photosynthetic capabilities.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A fertilizer comprising:
    at least one microbe selected from the group consisting of Trichoderma viride (NRRL B-50520), Scopulariopsis brevicaulis (NRRL B-50521), Scopulariopsis brevicaulis (NRRL B-50522), and combinations thereof and a substrate which is acted upon by the at least one microbe to release nitrogen.

2. The fertilizer of claim 1, wherein the substrate is a protein selected from the group consisting of feather, feather meal, and a derivative of urea.

3. The fertilizer of claim 1 further comprising:

a supplemental microbe in the form of a *Trichoderma* species.

4. The fertilizer of claim 1 further comprising:

a supplemental microbe selected from the group consisting of Piriformospora indica, a plant growth promoting rhizobacteria, mycorrhizal fungi, and combinations thereof.

5. The fertilizer of claim 1, wherein the fertilizer is in granule, pellet, dust, powder, slurry, film, and/or liquid suspension form.

6. The fertilizer of claim 1, wherein the fertilizer further comprises:

a nonproteinaceous binding agent selected from the group consisting of dextrans, starches, polyvinylchloride, and combinations thereof.

7. The fertilizer of claim 1, wherein the fertilizer further comprises:

a soluble nitrogen source selected from the group consisting of nitrate, ammonia, ammonium salts, amino acids, urea, fish meal or extract, compost extract, kelp extract, shrimp extract, shellfish extract, and combinations thereof.

8. The fertilizer of claim 1, wherein the fertilizer further comprises:

a source of phosphorus selected from the group consisting of rock phosphate, sodium phosphate, potassium phosphate, bone meal, and combinations thereof.

9. The fertilizer of claim 1, wherein the fertilizer further comprises:

a source of potassium selected from the group consisting of potassium chloride, potassium phosphate, potassium sulfate, Jersey green sand, organic sources of potassium, and combinations thereof.

10. The fertilizer of claim 1, wherein the fertilizer further comprises:

minor nutrients selected from the group consisting of salts, substances that contain iron, cobalt, manganese, magnesium, copper, calcium, boron, zinc, and combinations thereof.

11. The fertilizer of claim 1, wherein the fertilizer further comprises:

a growing media.

12. The fertilizer of claim 1, wherein the fertilizer further comprises:

a carrier selected from the group consisting of water, aqueous solutions, slurries, and powders.

13. The fertilizer of claim 1, wherein the fertilizer further comprises:

an additive selected from the group consisting of insecticide, fungicide, nematicide, additional organic fertilizer, bioinsecticide, biofungicide, bionematicide, agricultural or horticultural adjuvants, stickers, spreaders, surfactants, dispersants, humectants, UV protectants, and mixtures thereof.

14. The fertilizer of claim 1, wherein the fertilizer further comprises:

a source of organic carbon selected from the group consisting of compost and biochar.

15. A fertilizer comprising:

at least one microbe selected from the group of *Trichoderma viride* (NRRL B-50520), *Scopulariopsis brevicaulis* (NRRL B-50521), *Scopulariopsis brevicaulis* (NRRL B-505822), and combinations thereof and a keratin substrate which is acted upon by the at least one microbe to release nitrogen.

16. The fertilizer of claim 15 further comprising:

at least one microbe selected from the group consisting of *Streptomyces avermitilis, Streptomyces coelicolor, Streptomyces violaceoruber*, and combinations thereof.

17. The fertilizer of claim 15 further comprising:

a supplemental microbe in the form of a *Trichoderma* species.

18. The fertilizer of claim 15 further comprising:

a supplemental microbe selected from the group consisting of Piriformospora indica, a plant growth promoting rhizobacteria, mycorrhizal fungi, and combinations thereof.

19. The fertilizer of claim 15, wherein the fertilizer is in granule, pellet, dust, powder, slurry, film, and/or liquid suspension form.

20. The fertilizer of claim 15, wherein the fertilizer is in the form of a liquid suspension comprising amino acids and ammonia.

21. A method of enhancing growth of plants, the method comprising:

providing a fertilizer comprising:

at least one microbe selected from the group consisting of *Trichoderma viride* (NRRL B-50520), *Scopulariopsis brevicaulis* (NRRL B-50521), *Scopulariopsis brevicaulis* (NRRL B-50522), and combinations thereof and a substrate which is acted upon by the at least one microbe to release nitrogen; and contacting the fertilizer with plants or plant seeds under conditions effective to enhance the growth of the plants or plant seeds compared to plants or plant seeds to which the fertilizer was not applied.

22. A method of making a fertilizer comprising amino acids and ammonia, the method comprising:

providing at least one microbe selected from the group consisting of *Trichoderma viride* (NRRL B-50520), *Scopulariopsis brevicaulis* (NRRL B-50521), *Scopulariopsis brevicaulis* (NRRL B-50522), and combinations thereof;

providing a substrate which is acted upon by the at least one microbe to release nitrogen; and contacting the at least one microbe and the substrate under conditions effective to cause the at least one microbe to act on the substrate and produce a liquid suspension comprising amino acids and ammonia.

* * * * *